United States Patent [19]
Ichikawa et al.

[11] 4,073,818
[45] Feb. 14, 1978

[54] PROCESS OF PRODUCING ACENAPHTHENES

[75] Inventors: Hiroshi Ichikawa; Michio Sugimoto; Shigeyoshi Mizokami; Kosaku Honna; Hirozo Sugahara, all of Sodegaura, Japan

[73] Assignee: Idemitsu Kosan Co., Ltd., Tokyo, Japan

[21] Appl. No.: 782,038

[22] Filed: Mar. 28, 1977

Related U.S. Application Data

[63] Continuation-in-part of Ser. No. 661,731, Feb. 26, 1976, abandoned.

[51] Int. Cl.$^2$ .............................. C07C 15/20
[52] U.S. Cl. ...................... 260/668 F; 260/668 A; 260/668 D
[58] Field of Search ............ 260/668 A, 668 D, 668 F

[56] References Cited

U.S. PATENT DOCUMENTS

| | | | |
|---|---|---|---|
| 3,176,049 | 3/1965 | Crain et al. | 260/668 F |
| 3,565,964 | 4/1971 | Bushick et al. | 260/668 F |
| 3,884,986 | 5/1975 | Bushick et al. | 260/668 F |

FOREIGN PATENT DOCUMENTS

| | | | |
|---|---|---|---|
| 1,310,223 | 1/1962 | France | 260/668 F |

OTHER PUBLICATIONS

P. M. Pitts et al. Ind. and Engr. Chem. vol. 47, No. 1, pp. 770–773, 1955.
F. G. Ciapetta, Ind. and Engr. Chem. vol. 45, No. 1, pp. 159–161, 1953.
P. Schleyer, J. Am. Chem. Soc. 79, p. 3292, 1957.

*Primary Examiner*—Veronica O'Keefe
*Attorney, Agent, or Firm*—Flynn & Frishauf

[57] ABSTRACT

Acenaphthenes are obtained by reacting cyclododecatriene in the presence of a specified catalyst. Acenaphthenes are raw materials for jet fuel, synthetic resin, dye, bacteriocide, insecticide, synthetic lubricant oil, additives for various lubricating oils, etc.

15 Claims, 2 Drawing Figures

PROCESS OF PRODUCING ACENAPHTHENES

RELATED APPLICATION

This application is a continuation-in-part of our application Ser. No. 661,731, filed Feb. 26, 1976 now abandoned.

BACKGROUND OF THE INVENTION a. Field of the Invention

The present invention relates to a process for producing decahydroacenaphthene, octahydroacenaphthene, hexahydroacenaphthene, tetrahydroacenaphthene, acenaphthene and mixtures thereof (designated as "acenaphthenes" in the following) by reacting cyclododecatriene (designated as CDT in the following) in the presence of a catalyst.

b. Description of the Prior Art

Various methods for producing acenaphthenes have been developed. For example, it has been known that acenaphthenes can be produced from CDT which is prepared by trimerization of butadiene. In this method, acidic catalysts such as Lewis acids, mineral acids or organic acids, or catalysts consisting of inert alumina or Kieselguhr retaining the above-described acids have been used as catalysts, and especially phosphoric acid is used widely.

However, phosphoric acid used as a component of the catalyst causes environmental pollution and thus it is necessary to recover phosphoric acid completely from these catalysts. Moreover, when acenaphthenes are prepared from CDT using these acidic catalysts, low polymerized substances produced as by-products accumulate during the process. In order to remove such a substance, a process of calcining the catalyst is required, but regeneration of these acidic catalysts is practically impossible.

Further, these acidic catalysts are corrosive and especially, catalysts consisting of strong acid must be handled very carefully.

SUMMARY OF THE INVENTION

It is an object of this invention to provide a process of producing an acenaphthene.

In the process of this invention, CDT is reacted in the presence of a zeolite ion-exchanged with one or more metal ions selected from an alkaline earth metal, a metal of the manganese group and a rare earth metal as a catalyst.

DESCRIPTION OF THE PREFERRED EMBODIMENTS

Figure 1:
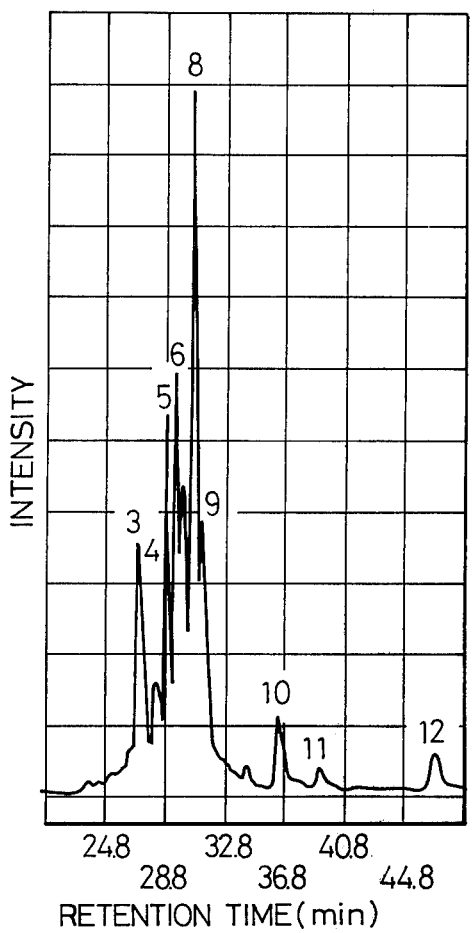

The present invention relates to a process of producing an acenaphthene. More particularly, this invention relates to a process of producing an acenaphthene by reacting CDT in the presence of a zeolite ion-exchanged with one or more kinds of metal ions selected from an alkaline earth metal, a metal of the manganese group and a rare earth metal as a catalyst.

In the present invention, the term "an acenaphthene" means decahydroacenaphthene, octahydroacenaphthene, hexahydroacenaphthene, tetrahydroacenaphthene, acenaphthene and mixtures thereof. Also, CDT means cyclododecatriene.

Catalysts employed in the present invention can be prepared by introducing a divalent or trivalent metal ion, especially an alkaline earth metal such as Mg, Ca, Sr, Ba, etc., a metal of the manganese group such as Mn, Re, etc., or a rare earth metal such as Y, La, Ce, Nd, Yb, etc., into a zeolite by contacting the zeolite with said metal in the form of an aqueous solution of a salt of the metal, and then drying and calcining the resulting zeolite. In this case, said metal or metals are not retained in the zeolite but are ion-exchanged with cation sites of the zeolite (such as $Na^+$, $K^+$, $NH_4^+$, etc.). Furthermore, metal ions or a combination of metal ions can be introduced into the zeolite by ion-exchange. It is preferable to treat a zeolite with said metal (or metals) in the form of an aqueous solution of a metal salt of an alkaline earth metal, a metal of the manganese group or a rare earth metal, such as $Ca(NO_3)_2$, $Mn(NO_3)_2$, $La(NO_3)_3$, etc. Moreover, in the case of a rare earth metal, a rare earth metal chloride for industrial use can also be employed.

Any type of zeolite can be employed for the present invention, but L-type, X-type and Y-type are preferred examples, and Y-type is the most preferable.

Ion-exchange rate is not limited; but it is preferable to be more than 20 percent in the case of $Na^+$-Y-type zeolite or $K^+$-Y-type zeolite, and to be more than 10 percent when $NH^+$-Y-type zeolite is used.

After drying a zeolite which has been subjected to ion-exchange, the zeolite is calcined by heating it in a stream of inert gas such as argon or nitrogen or in a dry air in order to enhance its catalytic activity. Temperature for calcining is preferably from 200° to 500° C. If the temperature is lower than 200° C., the calcining process is not carried out sufficiently, and if higher than 500° C., deterioration of catalyst may occur. Any shape of catalyst such as powder, particle, etc., can be utilized in this invention.

Reaction is performed at a temperature of from 200° to 400° C., preferably from 230° to 300° C., for 0.5 to 5 hours (in the case of a batch system) in the presence of the above-mentioned catalyst. Pressure for the reaction can be either atmospheric pressure or superatmospheric pressure. The reaction can be performed in a batch system or a continuous flow system.

The amount of catalyst is not limited. However, the catalyst is generally used in an amount expressed as from about 1.5 to 10 parts by weight of raw material, CDT, per weight of catalyst, preferably 2.5 to 7 in the case of a batch system. Expressed otherwise, from about 0.1 to about 0.7 part of catalyst is used per part of CDT.

Regeneration of catalyst can be attained by calcining it in a dry air. Conditions for calcining are preferably at a temperature of 400° to 500° C. for 5 to 8 hours.

According to the process of this invention, the catalysts employed show almost no corrosion and amounts thereof are less than the amounts used in the conventional methods. Furthermore, catalytic activity is higher and conversion yield and selectivity are also superior to those of the conventional methods. Moreover, life time of a catalyst is longer and it is very easy to regenerate the catalyst used. Catalyst of this invention will not be a cause of environmental pollution since harmful substances such as phosphoric acid are not present. Also, the catalysts can be used advantageously on an industrial scale, because the reaction can be performed in a continuous flow system.

Acenaphthenes obtained by the present invention can be utilized as raw materials for jet fuels, synthetic resins, dyes, bacteriocides and insecticides, and further they can also be widely utilized as raw materials for synthetic lubricating oils, additives for various lubricating oils, thermoresistant high polymers (such as polyesters, polyamides, etc.) and dimethyladamantane that is very useful starting material for medicines.

The present invention is illustrated in detail by the following typical examples.

EXAMPLE 1

To each 1 liter of an aqueous solution prepared by dissolving various amounts of $La(NO_3)_3.6H_2O$ or $Ca(NO_3)_2.4H_2O$ or $Mn(NO_3)_2.6H_2O$ into pure water, 10 grams of Y-type zeolite consisting of $SiO_2$ 63.5 weight percent (designated as "wt %" hereinunder), $Al_2O_3$ 23.5 wt % and $Na_2O$ 13.0 wt % (prepared by Union Carbide Co., "SK-40") or Y-type zeolite consisting of $SiO_2$ 65.0 wt % $Al_2O_3$ 23.0 wt %, $(NH_4)_2O$ 9.6 wt % and $Na_2O$ 2.4 wt % (prepared by Union Carbide Co., "SK-41") were added, respectively, and they were stirred for a prescribed time at 80° C.

Subsequently, they were filtered at room temperature (about 20° C.) and cakes thus obtained were washed thoroughly with pure water and then dried at 100° C. and finally calcined for 2 hours at 400° C. in a stream of dry air to obtain a powdered catalyst having a specific ion-exchange rate.

To a 100 ml stainless steel autoclave 10 grams of cyclododecatriene and 10 ml of n-hexane were added and then 2 grams of catalyst prepared by the method above described were quickly added and reacted for 2 hours at 270° C. After the reaction, the autoclave was cooled and catalyst was filtered off. Then product obtained from the filtrate by distilling n-hexane off was analysed by gas chromatography using p-xylene as an internal standard. Results are shown in Table 1. Gas chromatography was performed at 170° C. using Golay column Z-90.

| | |
|---|---|
| CDT conversion rate, % | 91.4 |
| yield of total acenaphthenes produced, % | 81.1 |
| yield of each product, % | |
| decahydroacenaphthene | 5.4 |
| octahydroacenaphthene | 87.1 |
| hexahydroacenaphthene | 2.8 |
| tetrahydroacenaphthene | 3.9 |
| acenaphthene | 0.8. |

The gas chromatogram of the product is shown by FIG. 1.

Identification of the products from analysis of gas chromatography and mass spectrum is given below.

| Substance | Peak No. of gas chromatogram | Mass spectrum (M/e) | |
|---|---|---|---|
| | | parent peak | fragment peak |
| | 3 | | |
| octahydro-acenaphthene | 4 | 162* | 133 |
| | 5 | | |
| CDT | 6 | 162 | 54 |
| octahydro-acenaphthene | 8 | 162 | 162, 133 |
| decahydro-acenaphthene | 10 | 164 | 121 |
| hexahydro-acenaphthene | 11 | 160 | 131 |
| tetrahydro-acenaphthene | 12 | 158 | 158 |

*Weak peak exists at 164 which corresponds to decahydroacenaphthene.

In the gas chromatogram, peak of a standard is found at a retention time of 18.8 minutes. The peak of acenaphthene is found at a retention time of from 56 to 60 minutes, but it is low and broad.

Accordingly, the term "Acenaphthene skeleton" is used to indicate the total acenaphthenes produced in the Table 1

| Conc. of Metal Ion (mol/l) | | Time of Ion Exchange Treatment (hr.) | Ion Exchange Rate (%) | Conversion Rate of CDT*³ (%) | Yield of Acenaphthene Skeleton (%) | Yield of Low Polymerized Substance (%) |
|---|---|---|---|---|---|---|
| $La^{3+}$ | 0.002 | 5 | 17.6 | 65.4 | 62.1 | 3.3 |
| | 0.004 | 6.5 | 29.0 | 81.4 | 57.0 | 24.4 |
| | 0.028 | 8 | 51.2 | 100 | 80.2 | 19.8 |
| | 0.210 | 15 | 58.5 | 96.3 | 82.4 | 13.8 |
| | 0.028*¹ | 10 | 72.3 | 90.9 | 62.4 | 28.5 |
| $Ca^{2+}$ | 0.003 | 6 | 22.4 | 89.8 | 78.5 | 11.3 |
| | 0.006 | 5 | 33.2 | 97.4 | 78.7 | 18.7 |
| | 0.1 | 10 | 62.2 | 91.4 | 81.1 | 10.7 |
| | 0.021*² | 6.5 | 90.6 | 94.0 | 81.3 | 12.7 |
| $Mn^{2+}$ | 0.003 | 6 | 14.6 | 100 | 70.4 | 29.6 |
| | 0.011 | 7 | 33.6 | 100 | 80.5 | 19.5 |
| | 0.045 | 15 | 47.5 | 100 | 72.4 | 27.6 |
| | 0.045 | 6 | 52.9 | 100 | 62.5 | 37.5 |
| | — | 8 | 85.0 | 100 | 79/6 | 20.4 |
| SK-40 not ion-exchanged | | — | — | | (No) | |

1) Sk-40 was subjected to ion-exchange with $La^{3+}$ and $Ca^{2+}$ and SK-41 was done with $Mn^{2+}$.

2) (a) Ion-Exchange Rate with $La^{3+}$, $Ca^{2+}$ = $\frac{\text{Amount of free Na}}{\text{Amount of Na in SK-40}} \times 100$ where amount of Na liberated from SK-40 was measured by atomic absorption spectrum.

(b) Ion-Exchange Rate with $Mn^{2+}$ = $\frac{\text{Moles of } Mn^{2+} \text{ consumed} \times 2}{\text{Moles of } (NH_4 + Na) \text{ in SK-41}} \times 100$ wherein concentration of $Mn^{2+}$ not ion-exchanged was measured by chelate titration method with 0.01 mol/liter of EDTA.

*¹those ion-exchanged with $La^{3+}$ at about 50% previously were ion-exchanged further with $La^{3+}$.
*²those ion-exchanged with $Ca^{2+}$ at about 50% previously were ion-exchanged further with $Ca^{2+}$.
*³Cyclododecatriene.

A gas chromatogram was obtained of the product obtained with the catalyst reported in Table 1 as $Ca^{2+}$ 0.1 mol/l. From the peak value in the gas chromatogram, conversion rate of cyclododecatriene (CDT) charge, yield of acenaphthene skeleton and yield of each product can be calculated. The results are as follows:

process. As indicated above, individual products can be isolated by chromatography. Other separation techniques such as distillation can be used.

Figure 2:
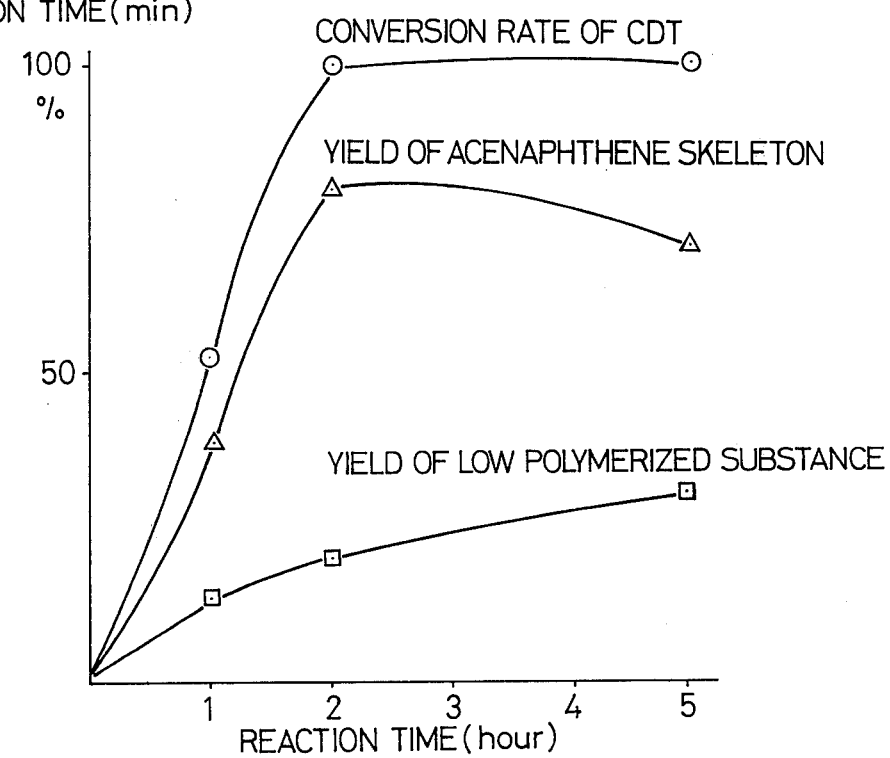

With a $La^{3+}$-Y type zeolite of the character shown in Table 1, the change in conversion rate and yield was plotted with reaction time. The concentration of $La^{3+}$ was 0.028 mol/l; time of ion exchange treatment was 8 hours and ion exchange rate was 51.2%. Reaction temperature was 270° C. and the weight ratio of CDT to catalyst was 5. Results are tabulated below in Table 2 and are shown graphically in FIG. 2.

Table 2

| | Reaction Time (hr.) | | |
|---|---|---|---|
| | 1 | 2 | 5 |
| conversion rate of CDT | 52.1% | 100% | 100% |
| yield of low polymerized substance | 13.6% | 19.8% | 29.9% |
| yield of acenaphthene skeleton | 38.5% | 80.2% | 70.1% |
| octahydroacenaphthene | 90.2% | 82.8% | 81.6% |
| decahydroacenaphthene | 5.7% | 5.3% | 6.8% |
| hexahydroacenaphthene | | 2.5% | 4.1% |
| tetrahydroacenaphthene | 4.1% | 8.5% | 6.3% |
| acenaphthene | ≈0% | 0.9% | 1.2% |

EXAMPLE 2

Experiments were carried out by the same method described in Example 1 except that SK-40 ion-exchanged with $La^{3+}$ (Ion-exchange rate is 51.2%) was used as a catalyst and the calcining temperature was 185°–500° C. Results are shown in Table 3.

Table 3

| Calcining Tem. (° C.) | Calcining Time (hr.) | Conversion Rate of CDT (%) | Yield of Acenaphthene Skeleton (%) | Yield of Low Polymerized Substance (%) |
|---|---|---|---|---|
| 185 | 2 | 100 | 79.9 | 20.1 |
| 300 | 2 | 100 | 85.5 | 14.5 |
| 400 | 2 | 100 | 80.2 | 19.8 |
| 500 | 2 | 69.1 | 57.7 | 11.4 |

EXAMPLE 3

Experiment was carried out by the same method described in Example 1 except that SK-40 ion-exchanged with $La^{3+}$ (Ion-exchange rate is 51%) was used as a catalyst and the reaction temperature, time and amount of catalyst were changed. Results are shown in Table 4.

Table 4

| Reaction Temperature (° C.) | Reaction Time (hr) | Amount of Catalyst (weight of Raw material/weight of catalyst) | Conversion Rate of CDT (%) | Yield of Acenaphthene Skeleton (%) | Yield of Low Polymerized Substance (%) |
|---|---|---|---|---|---|
| 230 | 2.0 | 5 | 40.4 | 37.4 | 3.0 |
| 250 | 2.0 | 5 | 77.7 | 65.4 | 12.3 |
| 272 | 2.0 | 5 | 100 | 80.2 | 19.8 |
| 300 | 2.0 | 5 | 100 | 65.2 | 34.8 |
| 270 | 1.0 | 5 | 52.1 | 38.5 | 13.6 |
| 270 | 5.0 | 5 | 100 | 70.1 | 29.2 |
| 270 | 2.0 | 1.5 | 100 | 55.0 | 45.0 |
| 270 | 2.0 | 2.5 | 100 | 75.2 | 24.8 |
| 270 | 2.0 | 10 | 58.9 | 52.1 | 6.8 |

EXAMPLE 4

To 1 liter of an aqueous solution of 0.02 Normal $Ca(NO_3)_2.4H_2O$, 10 grams of Y-type zeolite (Union Carbide Co.; "SK-41") consisting of $SiO_2$ 65.0 wt %, $Al_2O_3$ 23.0 wt %, $(NH_4)_2O$ 9.6 wt % and $Na_2O$ 2.4 wt % were added and stirred for 10 hours at 80° C. Subsequently, the zeolite-containing solution was filtered at room temperature and cakes thus obtained were washed with 1 liter of pure water. These processes were repeated twice.

The cakes obtained were added to 1 liter of an aqueous solution of 0.02 Normal $La(NO_3)_3.6H_2O$ and stirred for 10 hours at 80° C. After stirring, a series of procedures consisting of filtration at room temperature and washing with 1 liter of pure water was repeated three times.

The cakes thus obtained were placed in a porcelain boat after drying at 100° C. and then calcined for 2 hours in a stream of nitrogen gas (50 cubic centimeter/min.) at 300° C. with the temperature being increased from room temperature. As a result, catalyst powder was obtained. In the catalyst, $NH_4$ and Na of zeolite (SK-41) were ion-exchanged with La at 13% and with Ca at 2.4%, respectively.

To a reaction tube of 30 mm in diameter and 80 mm in length, 40 cubic centimeters (23 grams) of the catalyst which was obtained by the above process and was molded into a cylinder shape were packed. Reaction was performed at a temperature of 280° C. with a continuous flow system where cyclododecatriene was fed at a rate of 16.6 grams per hour and nitrogen gas at 4.36 liters per hour which were calculated at standard conditions. As a result, 15.9 – 16.1 grams of product were effused per 16.6 grams of cyclododecatriene and yield of acenaphthene skeleton in the product was more than 95%. Low polymer by-product adhered to the layer of the catalyst.

As decrease in catalytic activity was observed after 20 hours of the reaction, the used catalyst was calcined for 7 hours at 450° C. in a stream of dry air. The catalyst so regenerated had its original activity.

EXAMPLE 5

Using a zeolite catalyst subjected to ion-exchange and a catalyst not subjected to ion-exchange, an experiment was carried out as described in Example 1 in order to compare the catalytic activity of each. Results are shown in Tables 5 and 6.

Table 5

| Catalyst | Conversion Rate of CDT (%) | Yield of Acenaphthene Skeleton (%) | Yield of Low Polymerized Substance (%) |
|---|---|---|---|
| $La^{3+}$-X-type zeolite ($NH_4^+$) (Ion Exchange Rate: 83%) | 37.9 | 33.7 | 4.2 |
| $Ca^{2+}$-Y-type zeolite (SK-200) | 69.6 | 58.3 | 11.3 |
| Calcining Conditions: | 400° C. for 2 hours | | |
| Reaction Conditions: | 10 grams of Cyclododecatriene (CDT) 2 grams of Catalyst, 10 ml of n-hexane as a solvent | | |

Table 5-continued

| Catalyst | Conversion Rate of CDT (%) | Yield of Acenaphthene Skeleton (%) | Yield of Low Polymerized Substance (%) |
|---|---|---|---|
| | Temperature: 265° C. | Time: 2 hours | |

Table 6

| Catalyst | Conversion Rate of CDT (%) | Yield of Acenaphthene Skeleton (%) | Yield of Low Polymerized Substance (%) |
|---|---|---|---|
| X-type zeolite ($NH_4^+$ ion-exchange rate: 20.2%) | | (---No---) | |
| Zeolon ($H^+$ ion-exchange rate: more than 50%) | | (---No---) | |
| SK-41 ($NH_4^+$-Y-type zeolite ($Na^+$)) | 30.3 | 30.3 | — |
| $La^{3+}$-$Ca^{2+}$-Y-type zeolite ($Na^+$) (ion-exchange rate: more than 90%) | 64.3 | 51.4 | 12.9 |
| $Ce^{3+}$-Y-type zeolite (Na) (ion-exchange rate: 52.6%) | 61.5 | 52.4 | 9.1 |
| Calcining Conditions: | 400° C. for 2 hours | | |
| Reaction Conditions: | 10 grams of Cyclododecatriene, 2 grams of Catalyst, 10 ml of n-hexane as a solvent Temperature: 235° C.    Time: 2 hours | | |

As clearly shown in Tables 5 and 6, with a zeolite catalyst containing a monovalent cation ($H^+$-X-type, $H^+$-Zeolon, $NH_4^+$-Y-type) little or no reaction occurred, while the reaction rate increased extensively with the use of a zeolite catalyst containing a di- or tri-valent cation such as $Ca^{2+}$, $Mn^{2+}$, $La^{3+}$, $Ce^{3+}$, etc.

What is claimed is:

1. A process of producing an acenaphthene which comprises contacting a reaction charge consisting essentially of cyclododecatriene with a zeolite ion-exchanged with ions of one or more metals selected from the group consisting of an alkaline earth metal, a metal of the manganese group and a rare earth metal.

2. Process according to claim 1, wherein the acenaphthene comprises a mixture of decahydroacenaphthene, octahydroacenaphthene, hexahydroacenaphthene, tetrahydroacenaphthene and acenaphthene.

3. Process according to claim 1, wherein the reaction charge is so contacted at a temperature of 200° to 400° C.

4. Process according to claim 1, wherein from about 1.5 to about 10 parts by weight of cyclododecatriene is used per part by weight of catalyst.

5. Process according to claim 1, wherein the reaction is carried out in a batch system and the amount of cyclododecatriene is from 2.5 to 7 parts by weight per part by weight of catalyst.

6. Process according to claim 1, wherein the catalyst is a catalyst prepared by introducing ions of one or more metals selected from the group consisting of an alkaline earth metal, a metal of the manganese group and a rare earth metal into a zeolite by contacting said zeolite with said metal in the form of an aqueous solution of a salt of said metal, and then drying and calcining the resulting zeolite.

7. Process according to claim 6, wherein the zeolite is a L-type, X-type or Y-type zeolite.

8. Process according to claim 6, wherein the calcining step is carried out at a temperature of from 200° to 500° C.

9. Process according to claim 1, wherein the reaction is carried out in a continuous flow system.

10. Process according to claim 1, wherein the reaction charge contains n-hexane.

11. Process according to claim 1, wherein the acenaphthene is octahydroacenaphthene.

12. Process according to claim 1, wherein the acenaphthene is decahydroacenaphthene.

13. Process according to claim 1, wherein the acenaphthene is hexahydroacenaphthene.

14. Process according to claim 1, wherein the acenaphthene is tetrahydroacenaphthene.

15. Process according to claim 1, wherein acenaphthene is produced.

* * * * *

UNITED STATES PATENT AND TRADEMARK OFFICE
CERTIFICATE OF CORRECTION

PATENT NO. : 4,073,818
DATED : February 14, 1978
INVENTOR(S) : HIROSHI ICHIKAWA et al It is certified that error appears in the above-identified patent and that said Letters Patent are hereby corrected as shown below:

Columns 3-4, Table 1, fifth column, last line:

"(No)" as recited there should also be recited at the last line of the fourth and sixth columns.

Column 5, last line: replace "$4H_2D$" with ---$4H_2O$---.

Columns 3-4, Table 1, fifth column, last entry:
"79/6" should be -- 79.6 --.

Signed and Sealed this

Third Day of October 1978

[SEAL]

Attest:

RUTH C. MASON
Attesting Officer

DONALD W. BANNER
Commissioner of Patents and Trademarks